United States Patent
Okuda et al.

(10) Patent No.: US 10,881,558 B2
(45) Date of Patent: Jan. 5, 2021

(54) EVALUATION METHOD OF WEARING STATE OF DISPOSABLE DIAPER, EVALUATION SYSTEM OF WEARING STATE OF DISPOSABLE DIAPER, AND NON-TRANSITORY COMPUTER-READABLE STORAGE MEDIUM WITH A PROGRAM FOR EVALUATING WEARING STATE OF DISPOSABLE DIAPER

(71) Applicant: UNICHARM CORPORATION, Shikokuchuo-shi, Ehime (JP)

(72) Inventors: Jun Okuda, Kanonji (JP); Noritomo Kameda, Kanonji (JP); Takuya Miyama, Kanonji (JP)

(73) Assignee: UNICHARM CORPORATION, Ehime (JP)

(*) Notice: Subject to any disclaimer, the term of this patent is extended or adjusted under 35 U.S.C. 154(b) by 41 days.

(21) Appl. No.: 16/073,808

(22) PCT Filed: Nov. 9, 2016

(86) PCT No.: PCT/JP2016/083250
§ 371 (c)(1),
(2) Date: Jul. 30, 2018

(87) PCT Pub. No.: WO2017/134889
PCT Pub. Date: Aug. 10, 2017

(65) Prior Publication Data
US 2019/0060142 A1 Feb. 28, 2019

(30) Foreign Application Priority Data
Feb. 1, 2016 (JP) ................................ 2016-017121

(51) Int. Cl.
*A61F 13/84* (2006.01)
*A61F 13/49* (2006.01)
(Continued)

(52) U.S. Cl.
CPC ........ *A61F 13/84* (2013.01); *A61F 13/15203* (2013.01); *A61F 13/49* (2013.01);
(Continued)

(58) Field of Classification Search
None
See application file for complete search history.

(56) References Cited

U.S. PATENT DOCUMENTS 10,008,039 B1 * 6/2018 Neustein ............... G06T 19/006
2008/0132872 A1 * 6/2008 Trennepohl ....... A61F 13/15699
604/385.24

(Continued)

FOREIGN PATENT DOCUMENTS

| CN | 101031264 B | 4/2011 |
| CN | 104244891 A | 12/2014 |

(Continued)

OTHER PUBLICATIONS

Extended European Search Report in EP Application No. 16889372.5, dated Nov. 23, 2018, 6pp.
(Continued)

*Primary Examiner* — Wen W Huang
(74) *Attorney, Agent, or Firm* — Hauptman Ham, LLP

(57) ABSTRACT

An evaluation method of a wearing state of a disposable diaper including an elastic region in a waist portion or leg-surrounding portions, the evaluation method including: an evaluation image acquiring process in which a terminal including a photographing function acquires an image including at least a part of the elastic region as an evaluation image in the wearing state of the disposable diaper; and an evaluation process of evaluating the wearing state of the disposable diaper based on a degree of deformation of the evaluation image.

22 Claims, 10 Drawing Sheets

(51) Int. Cl.
*A61F 13/15* (2006.01)
*A61F 13/56* (2006.01)
*G06T 7/60* (2017.01)
*G16Z 99/00* (2019.01)

(52) U.S. Cl.
CPC .... *A61F 13/49011* (2013.01); *A61F 13/5633* (2013.01); *G06T 7/60* (2013.01); *A61F 2013/49093* (2013.01); *A61F 2013/8488* (2013.01); *A61F 2013/8491* (2013.01); *A61F 2013/8497* (2013.01); *G06T 2207/10004* (2013.01); *G16Z 99/00* (2019.02)

(56) References Cited

U.S. PATENT DOCUMENTS

| | | | |
|---|---|---|---|
| 2008/0310700 | A1 | 12/2008 | Fukusawa et al. |
| 2011/0208149 | A1* | 8/2011 | Vastag ............. A61F 13/49011 604/385.16 |
| 2011/0243425 | A1* | 10/2011 | Maltbie ............ A61F 13/15203 382/154 |
| 2012/0173249 | A1 | 7/2012 | Popp et al. |
| 2012/0220969 | A1* | 8/2012 | Jang ........................ A61F 13/42 604/361 |
| 2012/0232511 | A1* | 9/2012 | Velazquez ......... A61F 13/51394 604/372 |
| 2013/0143194 | A1* | 6/2013 | Agami ................. G06T 7/0004 434/365 |
| 2014/0372177 | A1 | 12/2014 | Agami et al. |
| 2015/0238367 | A1* | 8/2015 | Sakaguchi ........ A61F 13/15585 604/385.16 |

FOREIGN PATENT DOCUMENTS

| | | |
|---|---|---|
| JP | 2005-111175 A | 4/2005 |
| JP | 2008-532655 A | 8/2008 |
| JP | 2010-148731 A | 7/2010 |
| JP | 2011-30604 A | 2/2011 |
| JP | 2015-514521 A | 5/2015 |
| WO | 2008/021173 A2 | 2/2008 |

OTHER PUBLICATIONS

International Search Report in PCT Application No. PCT/JP2016/083250, dated Jan. 31, 2017, 4pp.
International Preliminary Report on Patentability in PCT Application No. PCT/JP2016/083250, dated Jan. 31, 2017, 22pp.
Office Action in EP Application No. 16889372.5, dated Jan. 23, 2020, 3pp.
Office Action in TW Application No. 105142509, dated Jul. 7, 2020, 15pp.
Office Action in CN Application No. 201680080814.8, dated Aug. 19, 2020, 10pp.
Office Action in EP Application No. 16889372.5, dated Oct. 1, 2020, 5pp.
Office Action in TW Application No. 105142509, dated Oct. 23, 2020, 3 pp.

* cited by examiner

| PRODUCT NAME | SIZE | Ps IN MAXIMUM STRETCHED STATE |
|---|---|---|
| PRODUCT A | S | a [cm] |
| | M | b [cm] |
| | L | c [cm] |
| PRODUCT B | S | d [cm] |
| | M | e [cm] |
| | L | f [cm] |
| * | * | * |
| * | * | * |
| * | * | * |

FIG. 7

EVALUATION METHOD OF WEARING STATE OF DISPOSABLE DIAPER, EVALUATION SYSTEM OF WEARING STATE OF DISPOSABLE DIAPER, AND NON-TRANSITORY COMPUTER-READABLE STORAGE MEDIUM WITH A PROGRAM FOR EVALUATING WEARING STATE OF DISPOSABLE DIAPER

RELATED APPLICATIONS

The present application is a national phase of International Application Number PCT/JP2016/083250, filed Nov. 9, 2016, which claims priority to Japanese Application Number 2016-017121, filed Feb. 1, 2016.

TECHNICAL FIELD

The present disclosure relates to an evaluation method of a wearing state of a disposable diaper, an evaluation system of a wearing state of a disposable diaper, and a non-transitory computer-readable storage medium with a program for evaluating a wearing state of a disposable diaper.

BACKGROUND ART

Disposable diapers are conventionally known as absorbent articles that absorb excreta such as urine. When these disposable diapers are used, a size adapted to the size of the body is selected to be fitted to the body with elastic members. PTL 1 describes a method of recognizing the degree of elasticity by visually specifying the degree of change of a display object (a picture of a rabbit) 9 incorporated in elastic members 8.

CITATION LIST

Patent Literature

[PTL 1] Japanese Unexamined Patent Application Publication No. 2005-111175

SUMMARY OF INVENTION

Technical Problem

However, in a disposable diaper 20 shown in PTL 1, since the degree of change of the display object 9 is visually observed, which means that the degree of elasticity is sensuously determined, there is a possibility that it may be difficult to determine whether the degree of elasticity of the elastic members 8 is appropriate or not.

The present disclosure has been made in view of the above circumstances and an objective thereof is to more precisely understand a wearing state of a disposable diaper.

Solution to Problem

A principal aspect of the present disclosure to achieve the above advantage is an evaluation method of a wearing state of a disposable diaper including an elastic region in a waist portion or leg-surrounding portions, the evaluation method including: an evaluation image acquiring process in which a terminal including a photographing function acquires an image including at least a part of the elastic region as an evaluation image in the wearing state of the disposable diaper; and an evaluation process of evaluating the wearing state of the disposable diaper based on a degree of deformation of the evaluation image.

Other features of the present disclosure will be made clear through the present specification with reference to the accompanying drawings present disclosure.

Advantageous Effects of Invention

According to the present disclosure, the wearing state of the diaper can be more precisely based on the degree of deformation of at least a part of the elastic region.

BRIEF DESCRIPTION OF DRAWINGS

FIG. 7 is a diagram illustrating data of a distance Ps between characteristic points s-s of a waist pattern in a maximum stretched state corresponding to each type of diaper.

DESCRIPTION OF EMBODIMENTS

Figure 1:
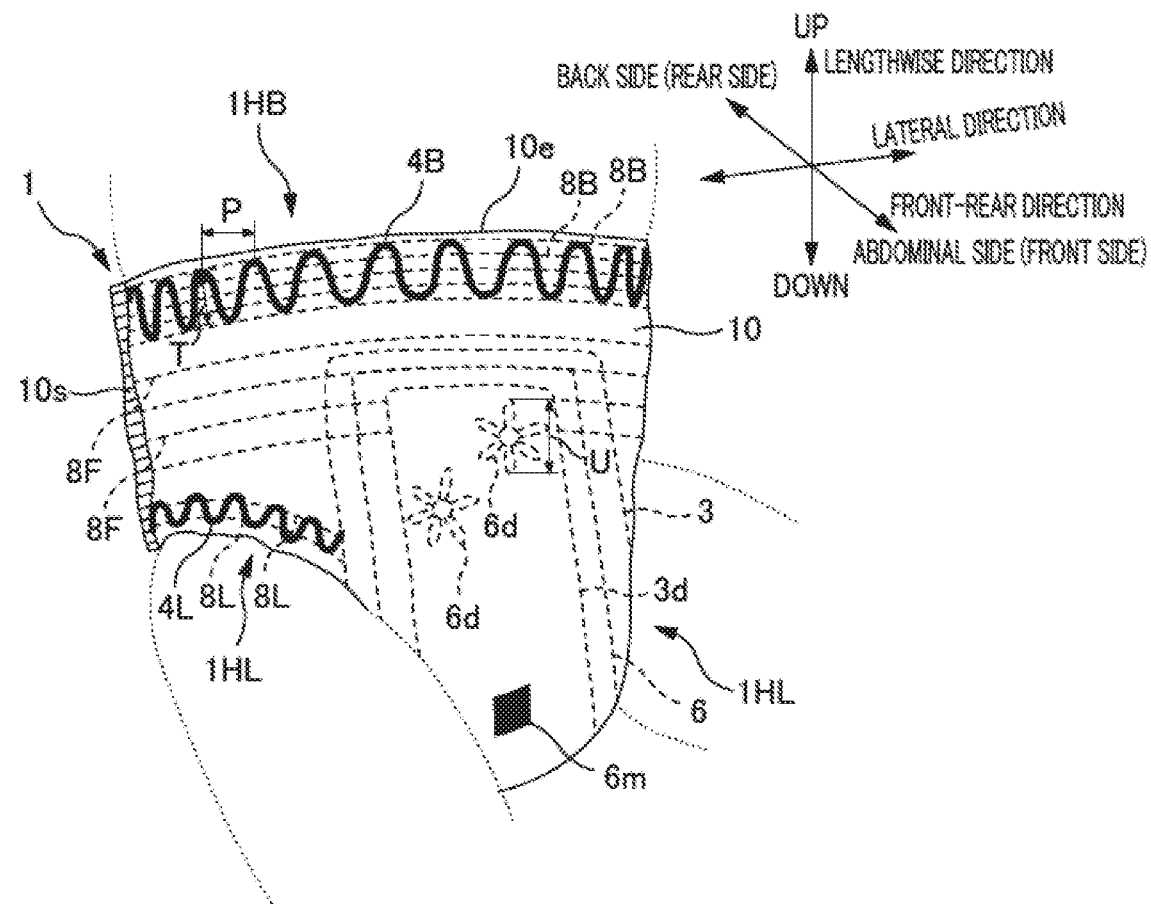
FIG. 1 is a perspective image view of a diaper 1 according to a first embodiment.

At least the following matters will be made clear by the description in the present specification and the accompanying drawings.

Disclosed is an evaluation method of a wearing state of a disposable diaper including an elastic region in a waist portion or leg-surrounding portions, the evaluation method including: an evaluation image acquiring process in which a terminal including a photographing function acquires an image including at least a part of the elastic region as an evaluation image in the wearing state of the disposable diaper; and an evaluation process of evaluating the wearing state of the disposable diaper based on a degree of deformation of the evaluation image.

According to such an evaluation method of a wearing state of a disposable diaper, the wearing state of the diaper can be understood more precisely based on the degree of deformation of at least a part of the elastic region.

In this evaluation method of a wearing state of a disposable diaper, it is preferable that a pattern is provided in at least a part of the elastic region, and the terminal acquires an image including at least a part of the pattern as the evaluation image in the evaluation image acquiring process.

According to such an evaluation method of a wearing state of a disposable diaper, the wearing state of the diaper can be understood more precisely based on the degree of deformation of a pattern provided in at least a part of the elastic region.

In this evaluation method of a wearing state of a disposable diaper, it is preferable that the disposable diaper includes a lengthwise direction and a lateral direction intersecting with the lengthwise direction, and the pattern is formed by repeating a predetermined design three times or more along the lateral direction.

According to such an evaluation method of a wearing state of a disposable diaper, for example, an average value of degrees of deformation of a plurality of evaluation images can be evaluated, and a part in which the evaluation image is easily acquired can also be increased, thus enabling the more precise understanding of the wearing state of the diaper.

In this evaluation method of a wearing state of a disposable diaper, it is preferable that the pattern is formed by repeating the predetermined design at a predetermined pitch, and the predetermined pitch is larger than a maximum pitch of wrinkles that are formed in the elastic region in a state in which the elastic region is contracted by a predetermined ratio with respect to a maximum stretched state.

According to such an evaluation method of a wearing state of a disposable diaper, the possibility that the pattern is hidden by wrinkles can be reduced.

In this evaluation method of a wearing state of a disposable diaper, it is preferable that elastic members are provided in the elastic region, and the pattern includes a plurality of colored portions provided in the elastic members.

According to such an evaluation method of a wearing state of a disposable diaper, it is possible to directly evaluate the degree of deformation of the elastic members.

In this evaluation method of a wearing state of a disposable diaper, it is preferable that the pattern has a predetermined length in the lengthwise direction of the disposable diaper.

According to such an evaluation method of a wearing state of a disposable diaper, since the size of the waist of the wearer is not necessarily constant, a pattern having a predetermined length in the lengthwise direction is provided, and thus the wearing state of the diaper can be more precisely understood.

In this evaluation method of a wearing state of a disposable diaper, it is preferable that the pattern including a first part that is disposed outside an absorbent body in the lateral direction of the disposable diaper, and the image including the first part as the evaluation image is acquired in the evaluation image acquiring process.

According to such an evaluation method of a wearing state of a disposable diaper, the degree of deformation of the elastic members can be more precisely evaluated.

In this evaluation method of a wearing state of a disposable diaper, it is preferable that the pattern including a second part that is disposed on an upper side of an absorbent body in the lengthwise direction of the disposable diaper, and the image including the second part as the evaluation image is acquired in the evaluation image acquiring process.

According to such an evaluation method of a wearing state of a disposable diaper, the degree of deformation of the elastic members can be more precisely evaluated.

In this evaluation method of a wearing state of a disposable diaper, it is preferable that the pattern including a third part that is disposed in each of upper portions of leg opening portions of the disposable diaper in the lengthwise direction of the disposable diaper, and the image including the third part as the evaluation image is acquired in the evaluation image acquiring process.

According to such an evaluation method of a wearing state of a disposable diaper, the possibility that the pattern is hidden by the legs of the wearer can be reduced.

In this evaluation method of a wearing state of a disposable diaper, it is preferable that the pattern includes a predetermined design, the predetermined design has a shape symmetric with respect to the lengthwise direction and the lateral direction of the disposable diaper in a state in which the elastic region is contracted by a predetermined ratio with respect to a maximum stretched state.

According to such an evaluation method of a wearing state of a disposable diaper, the wearing state of the disposable diaper is easily evaluated even by visually recognizing a predetermined design.

In this evaluation method of a wearing state of a disposable diaper, it is preferable that a picture pattern that can be visibly recognized through an exterior sheet is provided in a leak-proof sheet provided on a skin side of the exterior sheet disposed on the most non-skin side of the disposable diaper, and an image including at least a part of the picture pattern as the evaluation image is acquired in the evaluation image acquiring process.

According to such an evaluation method of a wearing state of a disposable diaper, the wearing state can be evaluated by using a picture pattern used for design.

In this evaluation method of a wearing state of a disposable diaper, it is preferable that the pattern is provided on an exterior sheet disposed on the most non-skin side of the disposable diaper, and a picture pattern that can be visibly recognized through the exterior sheet is provided on a leak-proof sheet provided on a skin side of the exterior sheet.

According to such an evaluation method of a wearing state of a disposable diaper, the pattern for evaluating the wearing state is easily distinguished from the picture pattern used for design.

In this evaluation method of a wearing state of a disposable diaper, it is preferable that, in the evaluation image acquiring process, another image including at least a part of the elastic region as another evaluation image is acquired after the image including the evaluation image is acquired, and a wearing state of the disposable diaper is evaluated based on degrees of deformation of the evaluation image and the other evaluation image.

According to such an evaluation method of a wearing state of a disposable diaper, for example, an influence due to meals can be reduced, and thus the wearing state can be evaluated more precisely.

In this evaluation method of a wearing state of a disposable diaper, it is preferable that an elapsed time since the wearer had a meal is acquired, and a wearing state of the disposable diaper is evaluated based on a degree of deformation of the evaluation image and the elapsed time.

According to such an evaluation method of a wearing state of a disposable diaper, an influence due to meals can be reduced.

In this evaluation method of a wearing state of a disposable diaper, it is preferable that evaluation information for each type is provided in the disposable diaper, the evaluation information being used for evaluating a wearing state of the disposable diaper for the each type of the disposable diaper, and a degree of deformation of the evaluation image is evaluated using the evaluation information in the evaluation process.

According to such an evaluation method of a wearing state of a disposable diaper, the evaluation in accordance with the type of disposable diaper in the wearing state is performed, and thus the wearing state of the disposable diaper can be evaluated more precisely.

In this evaluation method of a wearing state of a disposable diaper, it is preferable that a mark for specifying a type of the disposable diaper is provided in the disposable diaper, the terminal includes a mark image acquiring process that acquires a mark image including the mark, and a degree of deformation of the evaluation image is evaluated in the evaluation process by using the evaluation information corresponding to the type specified by the mark image.

According to such an evaluation method of a wearing state of a disposable diaper, the disposable diaper in the wearing state can be more easily specified, and thus the wearing state of the disposable diaper can be more precisely evaluated.

In this evaluation method of a wearing state of a disposable diaper, it is preferable that the pattern includes information for specifying a type of the disposable diaper, and the type of the disposable diaper is specified using the evaluation image.

According to such an evaluation method of a wearing state of a disposable diaper, the type of disposable diaper can also be specified by using the evaluation image.

In this evaluation method of a wearing state of a disposable diaper, it is preferable that the disposable diaper includes an absorbent main body, and in a thickness direction, the mark is provided at a position overlapping with the absorbent main body and a position in which an elastic member is not provided.

According to such an evaluation method of a wearing state of a disposable diaper, the possibility of changes of the shape of the mark due to elasticity of the elastic members can be reduced. Thus, the type of disposable diaper can be more precisely acquired.

In this evaluation method of a wearing state of a disposable diaper, it is preferable that the disposable diaper includes a lengthwise direction and a lateral direction intersecting with the lengthwise direction, the disposable diaper is an open-type disposable diaper including a first waist portion, a second waist portion and an absorbent main body, a fastening tape is provided in each end portion in the lateral direction in the second waist portion, a target region for allowing the fastening tape to be fastened is provided in the first waist portion, and it is evaluated in the evaluation process whether the fastening tape has been fastened to an appropriate position with respect to the target region based on a degree of deformation of the evaluation image.

According to such an evaluation method of a wearing state of a disposable diaper, it can be evaluated whether the fastening tapes are fastened at appropriated positions in the target region in an open-type disposable diaper by using the degree of deformation of the evaluation image. Accordingly, the disposable diaper can be worn more appropriately.

In this evaluation method of a wearing state of a disposable diaper, it is preferable that the disposable diaper includes a lengthwise direction and a lateral direction intersecting with the lengthwise direction, the disposable diaper is an open-type disposable diaper including a first waist portion, a second waist portion and an absorbent main body, a fastening tape is provided in each end portion in the lateral direction in the second waist portion, a target region for allowing the fastening tape to be fastened is provided in the first waist portion, an image including a fastening position of the fastening tape with respect to the target region as a fastening image is acquired, and a wearing state of the disposable diaper is evaluated in the evaluation process based on the fastening position specified by the fastening image and a degree of deformation of the evaluation image.

According to such an evaluation method of a wearing state of a disposable diaper, the wearing state of the disposable diaper can be appropriately evaluated based on the fastening position and the degree of deformation of the evaluation image.

An evaluation system of a wearing state of a disposable diaper including an elastic region in a waist portion or leg-surrounding portions, the evaluation system including: a terminal including a photographing function for acquiring an image including at least a part of the elastic region as an evaluation image in the wearing state of the disposable diaper, and an evaluation unit evaluating a wearing state of the disposable diaper based on a degree of deformation of the evaluation image.

According to such an evaluation system of a wearing state of a disposable diaper, the wearing state of the diaper can be understood more precisely based on the degree of deformation of at least a part of the elastic region.

A non-transitory computer-readable storage medium with a program for evaluating a wearing state of a disposable diaper including an elastic region in a waist portion or leg-surrounding portions, the program instructing a computer system including a terminal that has at least a photographing function to perform the following processes: a process to acquire an image including at least a part of the elastic region as an evaluation image in the wearing state of the disposable diaper; and a process to evaluate a wearing state of the disposable diaper based on a degree of deformation of the evaluation image.

According to such a non-transitory computer-readable storage medium with a program for evaluating a wearing state of a disposable diaper, the wearing state of the diaper can be understood more precisely based on the degree of deformation of at least a part of the elastic region.

First Embodiment

<<<Configuration of Disposable Diaper 1 According to First Embodiment>>>

Figure 2:
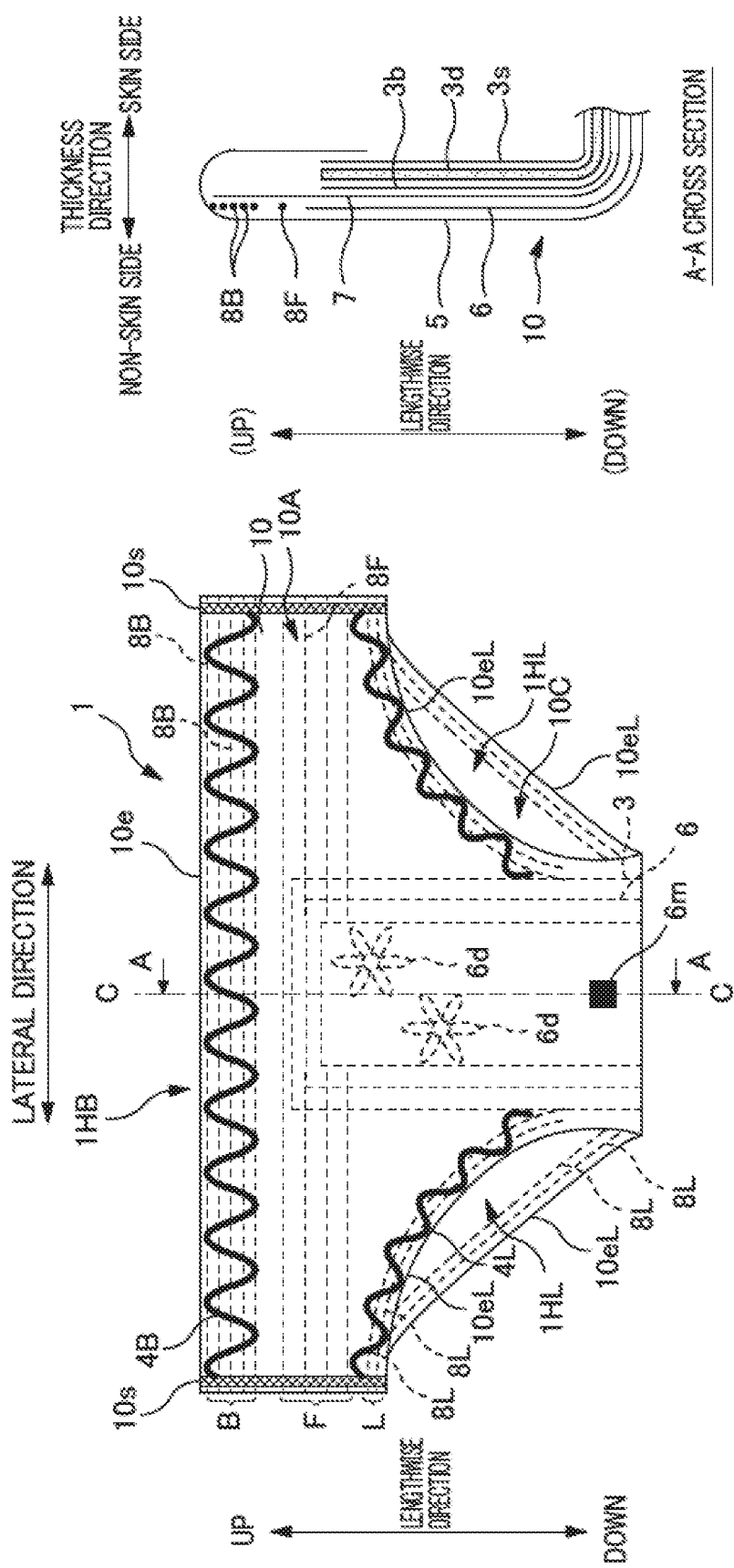
FIG. 2A is a schematic front view when the diaper 1 being in a stretched state is seen from an abdominal side.
FIG. 2B is a A-A cross-sectional view of FIG. 2A.

A configuration of a pull-on disposable diaper (hereinafter, also referred to as a "diaper 1") mainly for infants will be firstly described. FIG. 1 is a perspective image view of a diaper 1 according to a first embodiment, FIG. 2A is a schematic front view when the diaper 1 in a stretched state is seen from an abdominal side, and FIG. 2B is an A-A cross-sectional view of FIG. 2A. As illustrated in FIG. 1, FIG. 2A and FIG. 2B, the diaper 1 includes a "lengthwise direction", a "lateral direction" intersecting with the lengthwise direction, and a "thickness direction" intersecting with the lengthwise direction and the lateral direction. The "thickness direction" is also a front-rear direction when the diaper 1 is worn, and includes an "abdominal side" and a "back side". A line C-C of FIG. 2A shows a center in the lateral direction. It should be noted that the "stretched state" is a state in which the diaper 1 is stretched until it is free from wrinkles, and specifically, is a state in which a member (for example, an outer sheet 5) constituting the diaper 1 is stretched until the dimension of the member corresponds to a dimension of its member single body or until the dimension of the member becomes a length close to the member single body.

The diaper 1 includes an outer sheet 5 (also referred to as an "exterior sheet") positioned in a non-skin side of the wearer, and an inner sheet 7 overlapped on and joined to the outer sheet 5 from a skin side of the wearer in the thickness direction. The diaper 1 also includes a liquid-absorbent absorbent main body 3 that is overlapped on and joined to the inner sheet 7 from the skin side and absorbs excreta such as urine. The outer sheet 5 and the inner sheet 7 are made of nonwoven fabric, for example. Furthermore, as illustrated in FIG. 2B, the outer sheet 5 is configured so that an upper end part 10e thereof is folded to the skin side to cover an end region in the lengthwise direction of the absorbent main body 3. Hereinafter, by combining the outer sheet 5 and the inner sheet 7, it is also referred to as an exterior member 10.

The exterior member 10 forms an exterior shape of the diaper 1 in an opened state and has a substantially hourglass planar shape in plan view (not shown). The exterior member 10 is folded in two from the opened state by using a substantially center position in the lengthwise direction as a folding position, and end portions 10s, 10s in the lateral direction are formed by joining end portions of an abdominal side 10A in the lateral direction and end portions of a back side 10C in the lateral direction of the exterior member 10, thus forming a pull-on diaper 1 having a waist opening portion 1HB and a pair of leg opening portions 1HL.

The absorbent main body 3 has a substantially rectangular shape in plan view, and its longitudinal direction is placed at a center in the lateral direction from the abdominal side 10A to the back side 10C. The absorbent main body 3 includes an absorbent body 3d that absorbs liquid to hold it, a liquid-permeable surface sheet 3s that covers the absorbent body 3d from the skin side and allows excreta such as urine to be permeated, and a liquid-impermeable back face sheet 3b that covers the absorbent body 3d from the non-skin side and prevents liquid from leaking from the non-skin side. The absorbent body 3d is formed by shaping liquid absorbent fibers such as pulp fibers into a predetermined shape such as a substantially rectangular parallelepiped, and includes superabsorbent polymers therein. Further, barrier cuff portions that prevent lateral leakage may be provided in respective edges of the absorbent main body 3 in the lateral direction.

In the exterior member 10, a two-dimensional bar code mark 6m that specifies the type of disposable diaper is printed on the outer sheet 5 positioned so as to overlap with the absorbent main body 3. This mark 6m is printed by causing ink drops to be ejected from a printer such as a common ink-jet printer to the outer sheet 5 side and causing the ink to land in the exterior member 10.

A leak-proof sheet 6 that is smaller than the absorbent main body 3 and larger than the absorbent body 3d is disposed between the outer sheet 5 and the inner sheet 7 at the center of the diaper 1 in the lateral direction. The leak-proof sheet 6 is a liquid-impermeable sheet such as a film, thus enabling prevention of liquid leakage from the absorbent body 3d. Picture patterns 6d are printed on the respective non-skin sides of the abdominal side and back side of the leak-proof sheet 6, and such patterns make the impression of the diaper 1 soft and gorgeous. The picture patterns 6d of the leak-proof sheet 6 can be visually recognized through the outer sheet 5. Accordingly, the picture patterns 6d look slightly lighter in appearance than an after-mentioned waist pattern 4b and leg-surrounding patterns 4L, so that the picture patterns each having an impression that the outline became soft can be visually recognized. Thus, when the wearing state of the diaper is evaluated, it becomes easy to distinguish the picture patterns 6d from the waist pattern 4b and the leg-surrounding patterns 4L.

Elastic members 8 imparting elasticity to the diaper 1 are disposed at appropriated positions of the exterior member 10. As illustrated in FIG. 2A and FIG. 2B, elastic members (elastic strings) 8B, 8F and 8L are disposed so as to be interposed between the outer sheet 5 and the inner sheet 7. Regions in which each elastic member 8B, 8F, 8L are disposed constitute elastic regions B, F, L, respectively.

In upper end parts 10e, 10e in the lengthwise direction of the exterior member 10 (abdominal side 10A and back side 10C), a plurality of waist elastic members 8B, 8B are provided along the lateral direction, respectively. A part of the regions of the waist elastic members 8B, 8B is bonded and fixed to the outer sheet 5 and the inner sheet 7 while being stretched in the lateral direction to form a waist elastic region B imparting elasticity to the waist opening portion 1HB. This allows the diaper 1 to be fitted to the waist of the wearer and reduces a possibility of slip-down.

Figure 3:
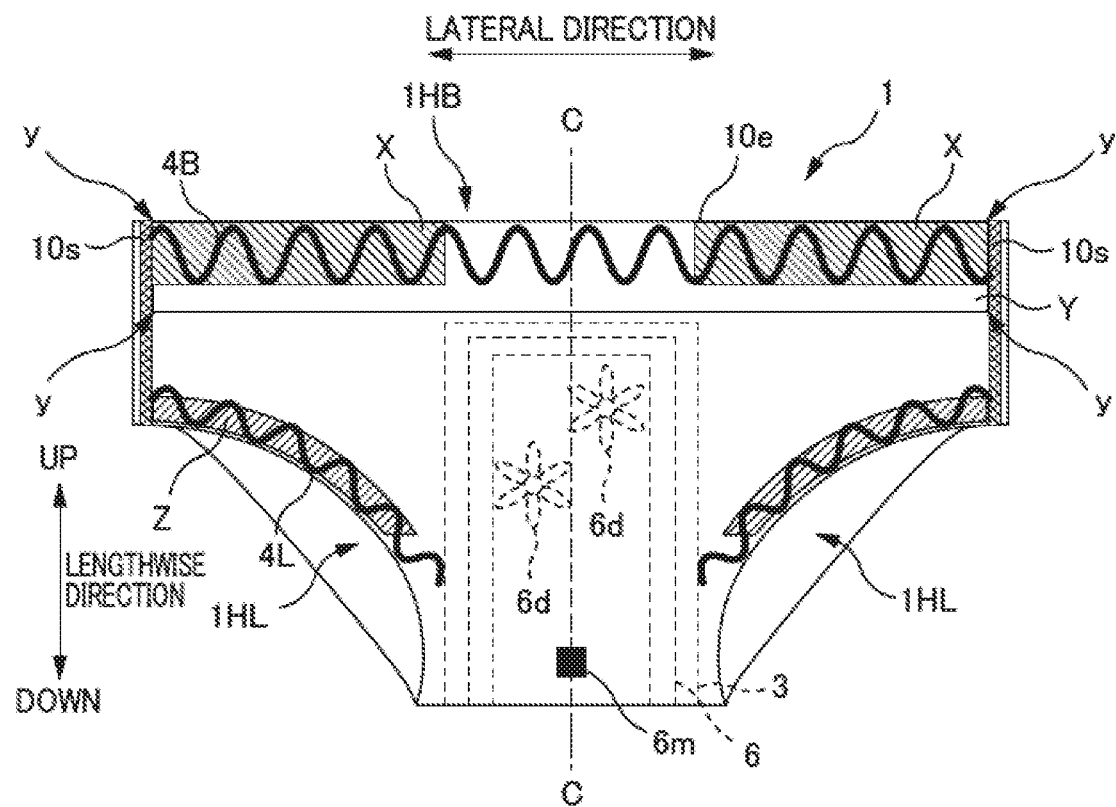
FIG. 3 is a diagram illustrating a waist pattern 4B and leg-surrounding patterns 4L of the diaper 1.

In the waist elastic region B, a waist pattern 4B is printed over the entire region in the lateral direction of the waist elastic region B, the waist pattern 4B being a wavy pattern alternately curved on the upper side and the lower side. The waist pattern 4B is used for evaluating the wearing state of the diaper 1. FIG. 3 is a diagram illustrating the waist pattern 4B and leg-surrounding patterns 4L of the diaper 1. FIG. 3 is an image view that has omitted the elastic members 8 or the like, and illustrates after-mentioned regions X, Y, Z with solid lines even though they are virtual regions. The waist pattern 4B is printed by causing ink drops to be ejected from a printer such as a common ink-jet printer to the outer sheet 5 side and causing the ink to land in the exterior member 10.

The waist pattern 4B is preferably printed on the outer side of the absorbent body 3d in the lateral direction of the diaper 1, and is more preferably printed on the outer side of the absorbent main body 3. In other words, the waist pattern 4B is preferably provided in a region X (a first part) shown in FIG. 3 (a part hatched with right-downward oblique lines shown in FIG. 3). Moreover, the waist pattern 4B is preferably printed on the upper side of the absorbent body 3d in the lengthwise direction, and is more preferably printed on the upper side of the absorbent main body 3. In other words, the waist pattern 4B is preferably provided in a region Y (a second part) in FIG. 3 (a rectangle area surrounded by lower-case letters y in FIG. 3). Accordingly, the waist pattern 4B is disposed in a part in which elasticity of the elastic members 8 are not limited by the absorbent body 3d, thus enabling a more precise evaluation of the degree of deformation of the elastic members.

A plurality of lower-waist elastic members 8F, 8F is provided along the lateral direction respectively, also in the lower side of the waist elastic region B in the lengthwise direction. A part of the lower-waist elastic members 8F, 8F is bonded and fixed to the outer sheet 5 and the inner sheet 7 while being stretched in the lateral direction to form a lower-waist elastic region F that imparts elasticity in the lateral direction to a region between the waist opening part 1HB and a lower part in the lengthwise direction.

Furthermore, a plurality of leg-surrounding elastic members 8L, 8L is provided at edge portions 10eL, 10eL that form the leg opening portions 1HL in edge portions of the exterior member 10, respectively. A part of the leg-surrounding elastic members 8L, 8L is bonded and fixed to the outer sheet 5 and the inner sheet 7 while being stretched along the edge portions 10eL, 10eL to form leg-surrounding elastic regions L that impart elasticity to the leg opening portions 1HL, 1HL. This can prevent the occurrence of a problem such as leakage of excreta to the outside of the diaper 1 from a clearance between the legs of a wearer and the leg opening portions 1HL.

In the leg-surrounding elastic region L, a leg-surrounding pattern 4L that is a wavy pattern alternatively curved upward and downward is printed in the same manner as the waist elastic region B. This leg-surrounding pattern 4L is preferably printed on an upper part of the leg opening portions 1HL in the abdominal side 10A or the back side 10C, and is preferably provided in a region Z (a third part) shown in FIG. 3 (a part hatched with left-downward oblique lines shown in FIG. 3). When the diaper 1 is worn, the lower parts of the leg opening portions 1HL may not be visually recognized due to the legs of the wearer. Thus, the leg-surrounding pattern 4L can be more easily visually recognized by providing it in the region Z.

<<<Evaluation Method of Wearing State of Diaper 1 According to First Embodiment>>>

In an evaluation method of a wearing state of the diaper according to the present embodiment, a caregiver or the like evaluates a wearing state of the diaper 1 of a wearer (infant) using a terminal 110. Hereinafter, a method of evaluating whether the type of diaper in the wearing state has been appropriately chosen, especially about sizes, by using the waist pattern 4B printed on the diaper 1 will be described. When the appropriate diaper has been chosen, the waist elastic members 8B in the diaper 1 properly fit the waist. However, when the type of diaper has been chosen incorrectly, the waist elastic members 8B may tightly fit the waist too much or the fitting to the waist may be insufficient.

<Evaluation System 100 of Wearing State of Diaper>

Figure 4:
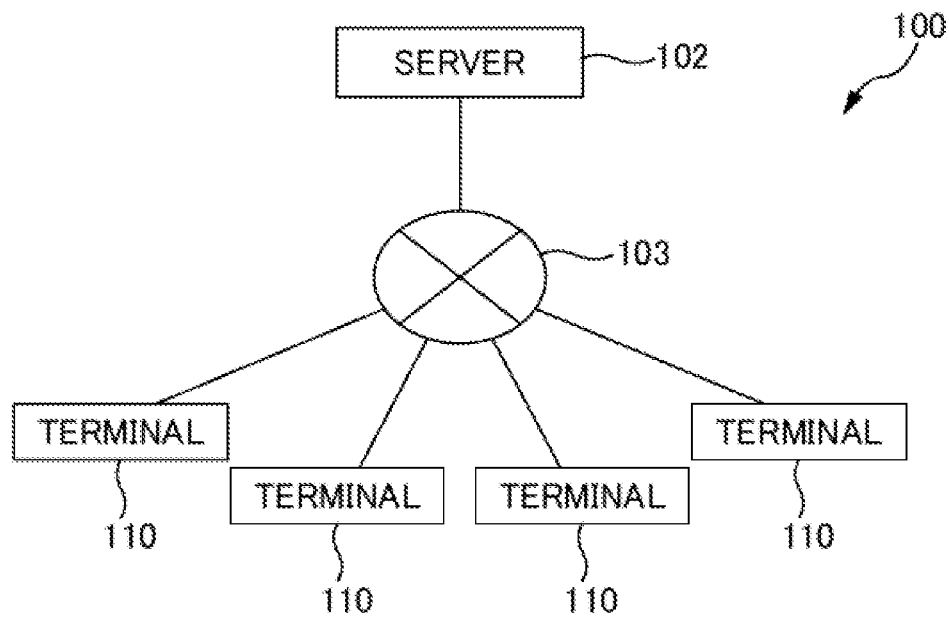
FIG. 4 is a diagram illustrating an overall configuration example of an evaluation system 100 of a wearing state of a diaper.

FIG. 4 is a diagram illustrating an overall configuration example of an evaluation system 100 of a wearing state of a diaper. The terminal 110 is, for example, a smartphone or a tablet terminal including a photographing function such as a camera, which can communicate with a server 102 through a wire or wireless network 103. The evaluation system 100 of the wearing state of the diaper sends an image of the wearer wearing the diaper 1, which has been acquired by the terminal 110, to the server 102 through the network 103, and the server 102 that performs an evaluation process as an evaluation unit sends an evaluation result to the terminal 110 to display it on the screen of the terminal 110. The evaluation method of the wearing state of the diaper will be described in detail below.

<Evaluation Method of Wearing State of Diaper>

Figure 5:
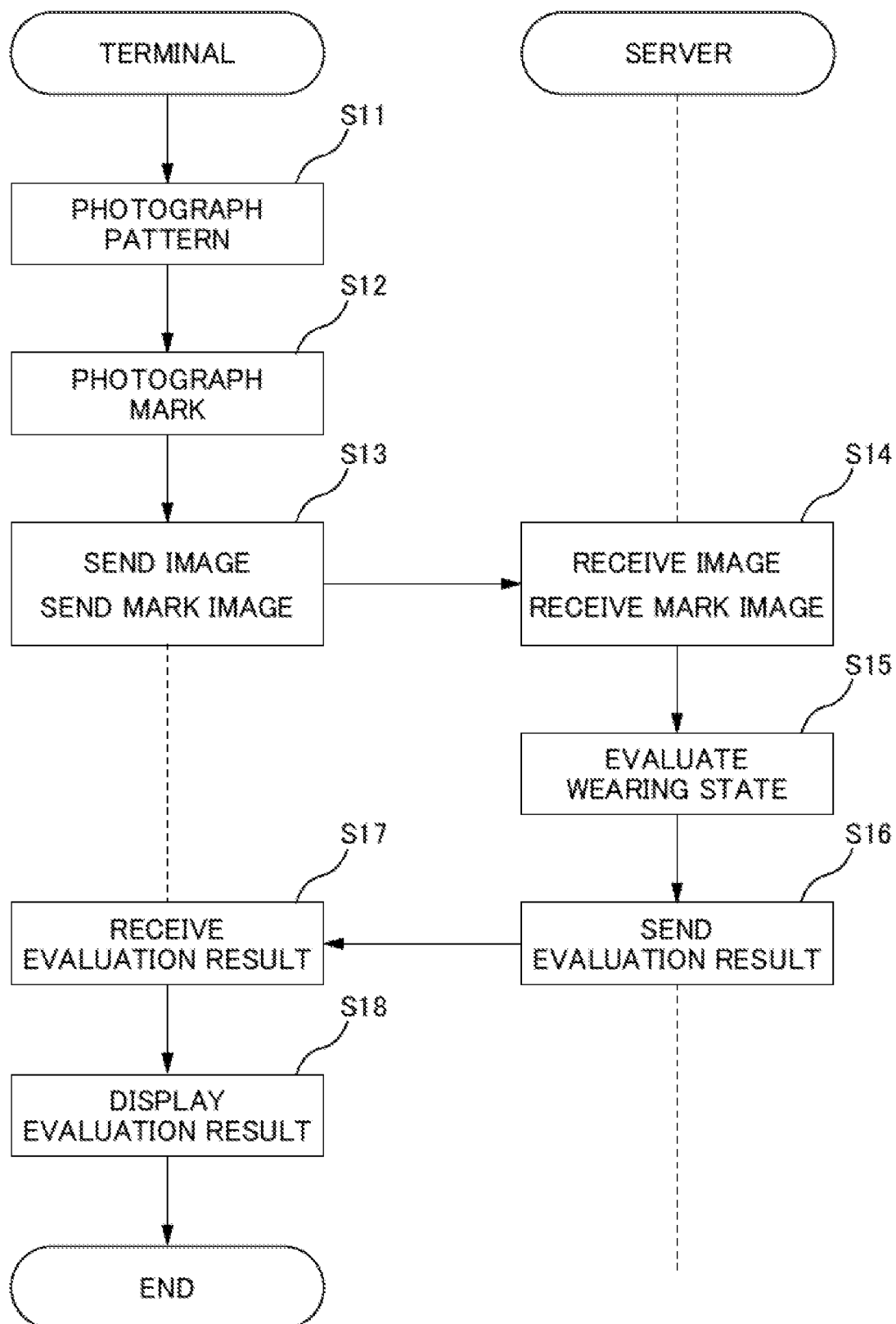
FIG. 5 is a diagram illustrating a flow of an evaluation method of a wearing state of a diaper in a present embodiment.

FIG. 5 is a diagram illustrating a flow of an evaluation method of a wearing state of a diaper in the present embodiment. First, the user of the terminal 110 photographs the diaper 1 worn by the wearer including the waist pattern 4B and the leg-surrounding patterns 4L from the side by using a camera (not shown) of the terminal 110 at the timing when the diaper of the wearer is exchanged with new one (S11, evaluation image acquiring process).

The waist pattern 4B and the leg-surrounding patterns 4L are preferably photographed from the side of the diaper 1. Specifically, the region X and the region Z on one side in the lateral direction of the diaper 1 shown in FIG. 3 are photographed. The evaluation of the wearing state of the diaper in the present embodiment is performed by evaluating the tightening condition of the waist elastic members 8B. However, if the elasticity of the elastic members 8 is limited by the absorbent body 3d and the absorbent main body 3, it becomes difficult to correctly evaluate the wearing state. Thus, in order to evaluate the degree of deformation of the elastic members 8 more precisely, it is preferable to photograph the diaper 1 from the side. In photographing the waist pattern 4B and the leg-surrounding pattern 4L, there is no need to photograph the entire area of the waist pattern 4B and the leg-surrounding pattern 4L, and it is sufficient to photograph at least a part of each waist pattern 4B and each leg-surrounding pattern 4L. At this time, a distance between one vertex and another vertex adjacent to the one vertex in the lateral direction on the upper side of a waveform of the waist pattern 4B of the diaper 1 in FIG. 1 is referred to as "P", and a distance in the lengthwise direction between an upper vertex and an lower vertex of the waveform is referred to as "T".

The distance in the photographed image differs from the actual distances (P, T) of the diaper 1. In the photographed image, a distance on the image between the one vertex and the other vertex adjacent to the one vertex in the lateral direction on the upper side of the waveform of the waist pattern 4B is referred to as "r", and a distance in the lengthwise direction on the image between the upper vertex and the lower vertex of the waveform is referred to as "t". The distance on the image can be determined by multiplying the size of one pixel by the number of pixels.

Then, the mark 6m of the diaper 1 is photographed from the abdominal (front) side of the diaper 1 by using the camera of the terminal 110 (S12, mark image acquiring process). By photographing this mark 6m from the front side of the diaper 1, identifiers such as two-dimensional bar codes can be more precisely read.

Next, the image of the diaper 1 in the wearing state including the waist pattern 4B and the leg-surrounding pattern 4L and the image of the diaper 1 in the wearing state including the mark 6m are sent to the server 102 through the network 103 (S13), and the server 102 receives these images (S14).

The server 102 evaluates the wearing state of the diaper 1 based on a pattern image as an evaluation image included in the image of the diaper 1 in the wearing state including the waist pattern 4B and the leg-surrounding pattern 4L, and a mark image as an evaluation image included in the image of the diaper 1 in the wearing state including the mark 6m (S15, evaluation process). This evaluation will be described later in detail.

The server 102 sends an evaluation result to the terminal 110 (S16), and the terminal 110 receives the sent evaluation result (S17). The terminal 110 displays the received evaluation result on the screen of the terminal 110 (S18), so that the user of the terminal 110 can know the evaluation of the wearing state of the diaper 1 of the wearer by seeing the screen of the terminal 110.

Figure 6:
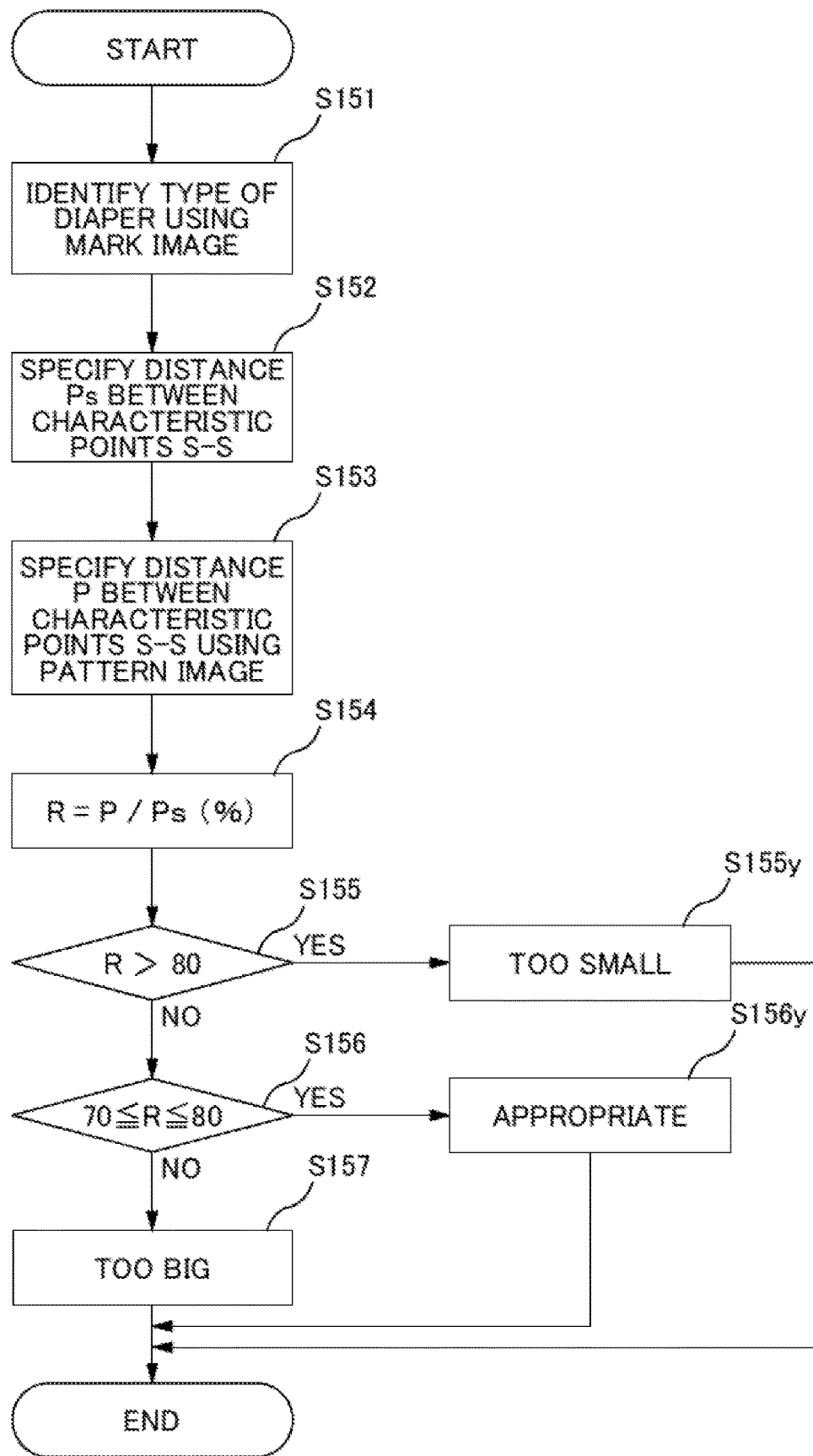
FIG. 6 is a diagram illustrating a flow of an evaluation method of a wearing state in a server 102.

In the following, the flow of the evaluation of the wearing state in the server 102 (S15) will be described. FIG. 6 is a diagram illustrating a flow of the evaluation method of the wearing state in the server 102. Here, an evaluation method using the pattern image of the waist pattern 4b out of the pattern images (evaluation images) will be described.

First, the server 102 uses the received mark image to specify the type of diaper (S151). "The type of diaper" as used herein refers to a size specified with respect to a specific product name, such as an M size of a "product A", in which the product A is a product name. A description follows regarding the evaluation method of the wearing state in a case in which the diaper 1 is an M size of the product A as an example.

Figure 8A:
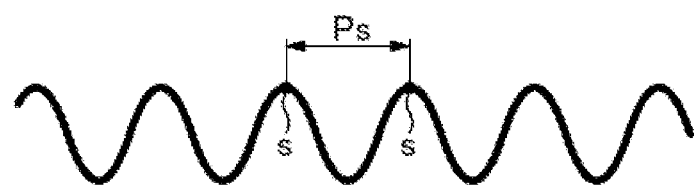
FIG. 8A is a diagram illustrating a distance Ps between characteristic points s-s in a maximum stretched state.

Then, a distance Ps between characteristic points s-s corresponding to the specified type of diaper is specified (S152). FIG. 7 is a diagram illustrating data of the distance Ps between the characteristic points s-s of the waist pattern in the maximum stretched state that responds to the type of diaper. FIG. 8A is a diagram illustrating the distance Ps between the characteristic points s-s in the maximum stretched state. Here, "the maximum stretched state" refers to a stretched state where each type of diapers is stretched until wrinkles disappear. In the waveform pattern of the present embodiment, a distance between one characteristic point s of the upper vertexes of the waveform and another characteristic point s adjacent to the one characteristic point s in the lateral direction is defined as P. In the server 102, pattern images (evaluation images), as illustrated in FIG. 8A, of each type of diaper in the maximum stretched state are stored. The distance Ps between the characteristic points s-s of the pattern image in this maximum stretched state is an indicator for calculating a degree of deformation of the pattern image described below. As illustrated in FIG. 7, when the diaper 1 of the present embodiment is an M size of the product A, the Ps in the maximum stretched state is b [cm]. Furthermore, the distance in the lengthwise direction from the upper vertex to the lower vertex of the waveform of the pattern image in the maximum stretched state is Ts. The distance Ps and the distance Ts are actual distance data.

Next, the distance P between the characteristic points s-s of the diaper 1 in the wearing state is specified by using the received pattern image (S153). The distance P of the diaper 1 can be calculated by P=r×(Ts/t). In other words, the distance P between the characteristic points s-s is calculated by using the distance t on the image and the distance Ts in the lengthwise direction in the maximum stretched state. In the present embodiment, the waist elastic members 8B are elastic strings having elasticity in the lateral direction and low elasticity in the lengthwise direction, thus allowing the waist elastic members 8B to be used for comparing the actual distance with the distance on the image.

A stretch ratio R of the diaper 1 is calculated by R=P/Ps (%) (S154) by using the calculated distance P to perform an evaluation based on the stretch ratio R. If the product is a M size of the "product A" in the present embodiment, the most appropriate stretch ratio R is 75%, and the range of the stretch ratio suitable for wearing is 70%≤R≤80%.

Figure 8B:
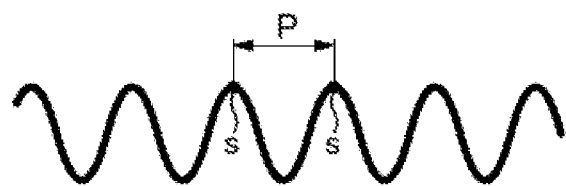
FIG. 8B is a diagram illustrating a distance P between the characteristic points s-s in the stretched state of 81%.

First, it is determined whether the ratio R is greater than 80% (S155). When the ratio R is greater than 80% (R>80 is YES), the elastic members 8 are greatly stretched more than the suitable stretch ratio for wearing, and accordingly, it is evaluated that the diaper 1 in the wearing state is "too small" (S155y). For example, FIG. 8B is a diagram illustrating the distance P between the characteristic points s-s in the stretched state of 81%. As illustrated in FIG. 8B, when the ratio R is 81%, the elastic members 8 are stretched too much, and the waist of the wearer may be excessively tightened. Thus, it is evaluated that the diaper 1 is "too small" for the wearer.

Figure 8C:
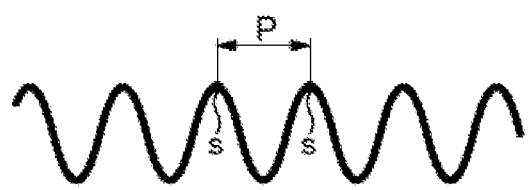
FIG. 8C is a diagram illustrating a distance P between the characteristic points s-s in the stretched state of 75%.

When the ratio R is less than 80% (R>80 is NO), it is determined whether the ratio R is 70%≤R≤80% (S156). When the ratio R is 70%≤R≤80% (70%≤R≤80% is YES), it is evaluated that the diaper 1 is "appropriate" because the stretch ratio of the diaper 1 is suitable for wearing (S156y). For example, FIG. 8C is a diagram illustrating the distance P between the characteristic points s-s in the stretched state of 75%. As illustrated in FIG. 8C, when the ratio R is 75%, the elastic members 8 are moderately stretched, and thus, it is evaluated that the diaper 1 is "appropriate" for the wearer.

Figure 8D:
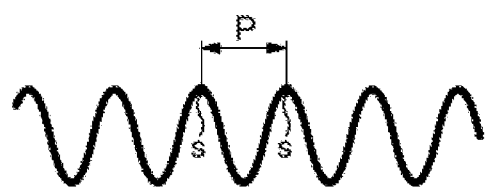
FIG. 8D is a diagram illustrating a distance P between the characteristic points s-s in the stretched state of 69%.

When the ratio R is not 70%≤R≤80% (70%≤R≤80% is NO), the ratio R is less than 70%, and the tightening around the waist is insufficient. Thus, it is evaluated that the diaper 1 in the wearing state is "too big" (S157). For example, FIG. 8D is a diagram illustrating the distance P between the characteristic points s-s in the stretched state of 69%. As illustrated in FIG. 8D, when the ratio R is 69%, the tightening around the waist due to the elastic members 8 is insufficient. Accordingly, the diaper 1 may not appropriately fit the waist of the wearer. Thus, it is evaluated that the diaper 1 is "too big" for the wearer.

The server 102 sends any one of "too small" (S155y), "appropriate" (S156y), or "too big" (S157) to the terminal 110 as an evaluation result (S16), and thus the user of the terminal 110 can easily know whether the size of the diaper 1 is suitable or not for the wearer.

In the evaluation of the wearing state by the server 102 (S15), the server 102 may receive a plurality of pattern images and make an evaluation from an average value of respective calculated results. Especially for infants, the size of the waist remarkably changes before and after the meal, and accordingly, if only the results immediately after exchanging the diaper are used, a bias may occur. For example, even if the evaluation of the wearing state of the diaper is "too small" immediately after the meal, there is a case where it is evaluated that the diaper 1 is "appropriate" when the infant is hungry. In order to reduce variations of such evaluation results, the evaluation may be made by using an average value of respective stretch ratios of the pattern image immediately after the meal and the pattern image after one hour has passed since the meal. Furthermore, the evaluation may be made by an average value of the calculated results using the pattern images at predetermined time intervals such as not only a meal time, but also at the time of exchanging the diaper, one hour after the diaper exchange or the like. Accordingly, the wearing state of the diaper can be evaluated more precisely.

Moreover, an elapsed time since the wearer had a meal is inputted into the terminal 110 by using a predetermined program or the like, and the input results are sent to the server 102, so that the server 102 may correct the changes in the size of the waist due to meals. This can reduce influence caused by changes in the waist portion due to meals.

The waist pattern image has been described as an evaluation image in the above. In addition, the same applies to a leg-surrounding pattern image. Since the waist elastic region is a part where the degree of elasticity most largely changes in the diaper 1, the wearing state of the diaper can be evaluated more precisely by using the waist pattern 4B to evaluate the wearing state. Furthermore, the wearing state is evaluated by the degree of elasticity of the leg-surrounding pattern 4L, thus enabling the evaluation of the wearing state without being affected by changes in waist due to meals or the like. Accordingly, the evaluation may be made by using only either one of the waist pattern 4B or the leg-surrounding pattern 4L, or, the evaluation may be made by using both the waist pattern 4B and the leg-surrounding pattern 4L. Even more accurate evaluation of the wearing state can be made by using both of them.

<Pattern>

The waist pattern 4B is preferably formed by repeating a predetermined design three times or more along the lateral direction. The waist pattern 4B of the present embodiment is a wavy pattern curving in an up-down direction, and is formed by repeating a design three times or more along the lateral direction, the design being made of a curved line provided between the characteristic point s that is an upper vertex and the characteristic point s that is an upper vertex adjacent to the prior characteristic point s in the lateral direction as shown in FIG. 2A or the like. This can acquire the distance P between the characteristic points s-s at two or more points, and the determination of the average value of these two or more P values can result in an acquisition of the more precise degree of deformation of the elastic member. It should be noted that the leg-surrounding pattern 4L is also preferably formed by repeating a predetermined design three times or more.

Moreover, the waist pattern 4B and the leg-surrounding pattern 4L are preferably formed by repeating a larger design than the maximum pitch of wrinkles formed in the exterior member 10 due to the elastic members 8. This can reduce the possibility that the design is hidden by wrinkles formed in the exterior member 10, and evaluate the wearing state of the diaper more easily and precisely.

The waist pattern 4B and the leg-surrounding pattern 4L each preferably have a predetermined length not only in the lateral direction but also in the lengthwise direction. By providing the reference points s at the upper vertex and the lower vertex of the waveform, differences in the degree of elasticity between the elastic members 8 in the lengthwise direction can be corrected. For example, the average values of the distance between the upper vertexes and the distance between the lower vertexes are calculated, and then these average values may be compared with the foregoing distance Ps. In particular, the shape of the waist of an infant is rounded when seen from the lateral direction, and thus apart in which the elastic members 8 stretch too much and a part in which the elastic members 8 does not stretch may occur even in the up-down direction in the waist elastic region B. Thus, by providing the waist pattern 4B and the leg-surrounding pattern 4L each having a predetermined length also in the lengthwise direction, a bias in the degree of elasticity in the lengthwise direction is taken into consideration, and thus the wearing state of the diaper can be evaluated more precisely.

Figure 9A:
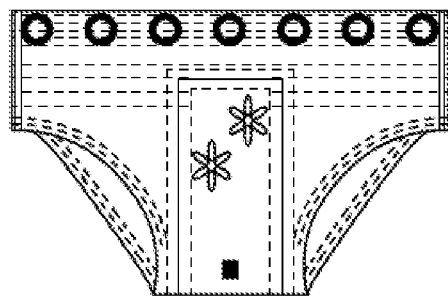
FIG. 9A is a diagram illustrating a waist pattern made of a plurality of circular designs.
Figure 9B:
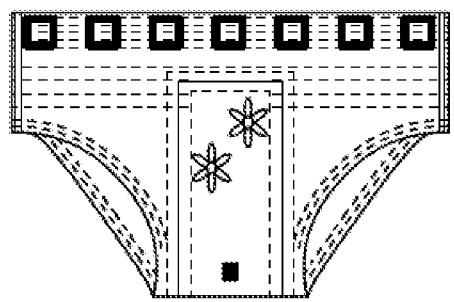
FIG. 9B is a diagram illustrating a waist pattern made of a plurality of square-shaped designs.
Figure 9C:
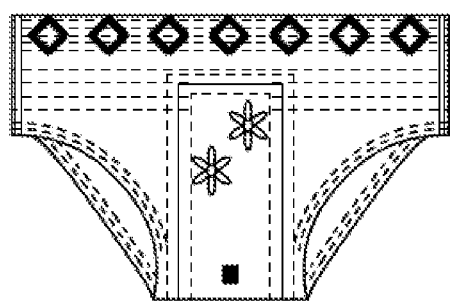
FIG. 9C is a diagram illustrating a waist pattern made of a plurality of rhombus-shaped designs.

Further, in the waist pattern 4B and the leg-surrounding pattern 4L, each design is not necessarily continuous. Each design may be repeated at predetermined intervals. FIG. 9A, FIG. 9B and FIG. 9C illustrate another example of the waist pattern 4B. FIG. 9A is a diagram illustrating a waist pattern made of a plurality of circular designs, FIG. 9B is a diagram illustrating a waist pattern made of a plurality of square-shaped designs, and FIG. 9C is a diagram illustrating a waist pattern made of a plurality of rhombus-shaped designs. In FIG. 9A, FIG. 9B and FIG. 9C, the diaper 1 is in a stretched state of 75% with respect to the maximum stretched state. The diaper 1 becomes the most appropriate wearing state when the diaper 1 is in the stretched state of 75%.

In FIG. 9A, the plurality of circular designs is arranged at predetermined intervals along the lateral direction. In FIG. 9B, the plurality of square-shaped designs is arranged at predetermined intervals along the lateral direction. In FIG. 9C, the plurality of rhombus-shaped designs is arranged at predetermined intervals along the lateral direction. As illustrated in FIG. 9A, FIG. 9B and FIG. 9C, each design has a shape symmetric with respect to the lengthwise direction and the lateral direction in the 75% contracted state. That is, in the stretched state of 75%, the design in FIG. 9A becomes a perfect circle, the design in FIG. 9B becomes a square, and the design in FIG. 9C becomes a rhombus having an internal angle of 90°. Accordingly, if the state of each pattern is close to the state illustrated in FIG. 9A, FIG. 9B, or FIG. 9C even before using the terminal 110, the appropriate wearing state of the diaper 1 can be visually recognized. Furthermore, even if the wearing state cannot be decided visually, the appropriate evaluation can be obtained by acquiring the evaluation result from the server 102, thus enabling the wearing state of the diaper to be appropriate.

Second Embodiment

<<<Configuration of Disposable Diaper 2 According to Second Embodiment>>>

Figure 10:
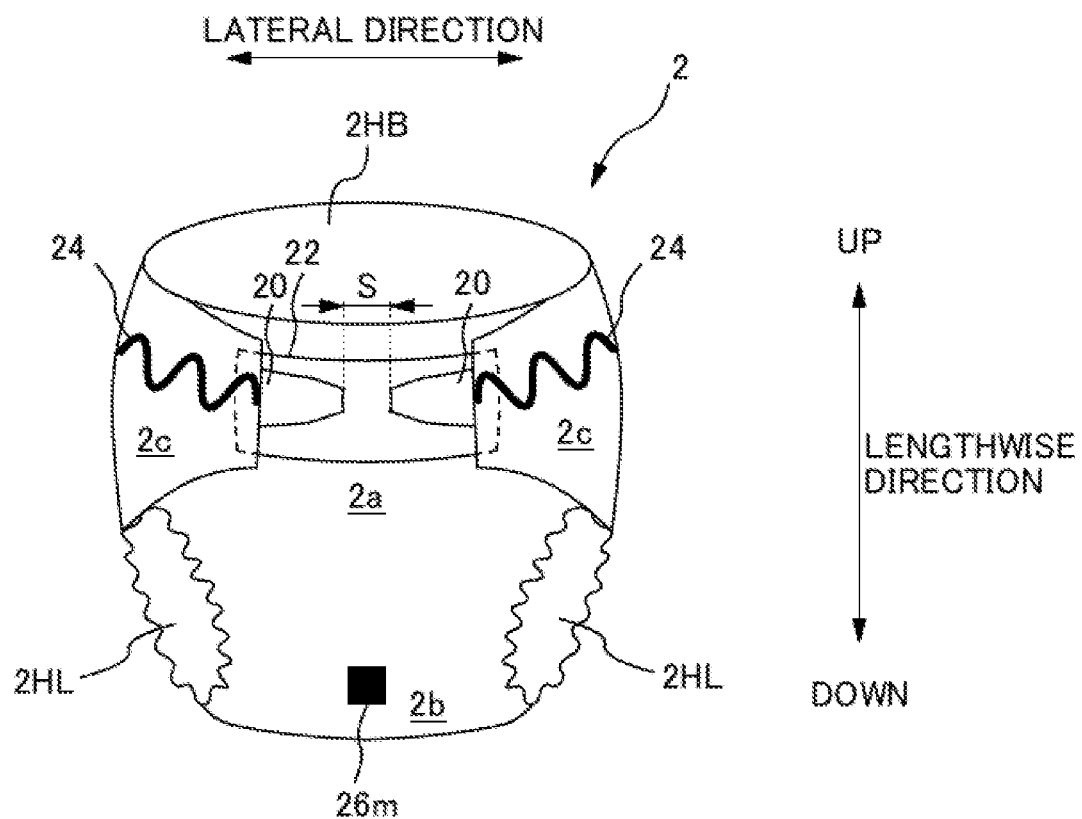
FIG. 10 is an image view of a diaper 2 according to a second embodiment.

In a second embodiment, a case of using a tape-type disposable diaper (hereinafter, also referred to as a "diaper 2") mainly intended to be worn by infants will be described. FIG. 10 is an image view of the diaper 2 according to the second embodiment.

The diaper 2 includes a longitudinal direction, a lateral direction, and a thickness direction that are orthogonal to one another, and includes a front waist region 2a covering the abdominal side portion of the wearer, a back waist region 2c covering the back side portion, and a crotch region 2b positioned between the front waist region 2a and the back waist regions 2c.

The diaper 2 includes an absorbent main body between a liquid-permeable inner sheet and a liquid-impermeable outer sheet. The absorbent main body is disposed from the front waist region 2a to the back waist region 2c in the longitudinal direction, and includes an absorbent body that absorbs and holds excreta, and a liquid-permeable covering material that covers the absorbent body. Moreover, a plurality of elastic strings (not shown) extensible in the lateral direction are provided in the back waist region 1c to improve a fitting property around the waist, and the region in which the elastic strings are provided is referred to as a back waist elastic region.

In the back waist elastic region, a back waist pattern 24 that is a wavy pattern curving upward and downward alternatively is printed on the most non-skin side of the back waist region 2c over the entire region from one end to the other end of the back waist region 2c in the lateral direction. The back waist pattern 24 is used for evaluating the wearing state of the diaper 2. The back waist pattern 24 is printed on the non-skin side of the exterior member using a printer such as an inkjet printer, in the same manner as the waist pattern 4B and the leg-surrounding pattern 4L in the first embodiment.

On the non-skin side of the outer sheet in the crotch region 2b, a mark 26m such as a two-dimensional bar code that specifies the type of the disposable diaper is printed in the same manner as the first embodiment. This mark 26m is preferably printed on a part in which the elastic members are not placed in the crotch region 2b so as to be more accurately read.

In back waist region 2c, a pair of fastening tapes 20 extending to both outer sides in the lateral direction is provided. On the non-skin side surface of the exterior sheet in the front waist region 1a, a target region 22 having a rectangular planar shape is provided, and the fastening tapes 20 is configured to be capable of being fastened to and detached from the target region 22.

When the diaper 2 is worn, the diaper 2 is first folded in two in the longitudinal direction while being brought into contact with the wearer, and then a pair of fastening tapes 20 and its peripheral portions are folded toward the center side in the width direction to fasten the pair of fastening tapes 20 to the target region 22 in the front waist region 2a. Accordingly, as illustrated in FIG. 10, the waist opening portion 2HB and a pair of leg opening portions 2HL are formed. It should be noted that the diaper 2 may also include a barrier cuff (not shown) or the like, appropriately.

<<<Evaluation Method of Wearing State of Diaper 2 According to Second Embodiment>>>

An evaluation method of a wearing state of the diaper 2 according to the present embodiment evaluates a wearing state of the diaper 2 worn by an infant who is a wearer by using the terminal 110 possessed by a caregiver or the like of the wearer in the same manner as the first embodiment. A description follows regarding a method of evaluating the wearing state of the diaper 2 by using the back waist pattern 24 printed in the diaper 2. In the present embodiment, it is evaluated whether the diaper 2 has been worn at a proper position, and whether the size of the diaper 2 is appropriate. In the following description, the elements in common with those in the first embodiment will be denoted by the same reference numerals.

First, the diaper 2 in the wearing state including the back waist pattern 24 is photographed by using a camera of the terminal 110 in the same manner as the first embodiment. Infants wearing tape-type disposable diapers such as the diaper 2 are often in a sleeping state, and thus photographing the back side portion of the diaper may be difficult. Accordingly, photographing the diaper from the side, which can be photographed even when the wearer sleeps, is preferable.

Then, the diaper 2 including target tapes 20, the target region 22 and the mark 26$m$ is photographed from the abdominal side (front side) by using the camera of the terminal 110. At this time, not only the mark 26$m$ but also the target tapes and the target region 22 are photographed simultaneously. This can save time and reduce the amount of information to be sent to the server 102.

The terminal 110 sends, through the network 103, an image of the diaper 2 in the wearing state including the back waist pattern 24, and an image of the diaper 2 including the target tapes 20, the target region 22 and the mark 26$m$, and then the server 102 receives them.

The server 102 evaluates the wearing state of the diaper 2 based on a pattern image included in the image of the diaper 2 in the wearing state including the back waist pattern 24, a tape position image and a mark image included in an image of the diaper 2 including the target tapes 20, the target region 22 and the mark 26$m$.

The server 102 firstly specifies the type of diaper by using the mark image in the same manner as the first embodiment. When the type of diaper is specified, the diaper 2 is opened to specify a length T that is a length from the lateral end of the target tape 20 on one side to the lateral end of the target tape 20 on the other side in the lateral direction in the stretched state. A description follows regarding a case in which the diaper 2 is a product E having an M size and a length T of k [cm] as an example.

A distance Ps2 between the characteristic points in the back waist pattern image in the maximum stretched state of the product E having an M size is specified in the same manner as the first embodiment. This distance Ps2 is a specified reference value obtained by specifying the type of diaper, and is a distance between the characteristic points s-s in the back waist pattern image in the maximum stretched state.

Next, a distance P2 between the characteristic points of the diaper 2 in the wearing state is specified by using the received pattern image, and the stretch ratio R of the diaper 2 is calculated by R=P2/Ps2 (%). The most proper stretch ratio of the product E having a M size is a case of R=75%, and a range of the stretch ratio suitable for wearing is 70%≤R≤80%. For this reason, it can be found that, when the ratio R is greater than 80% (R>80%), the elastic members in the back waist region 2$c$ are excessively stretched, and when the ratio R is less than 70% (R<70%), the elastic members in the back waist region 2$c$ do not stretch appropriately.

Then, a distance S from the lateral end of one fastening tape 20 to the lateral end of another fastening tape 20 is specified by using the received tape position image, each fastening tape being fastened in the target region 22 of the diaper 2 in the wearing state. This distance S becomes a value within a predetermined range (h<S<j, h and j being positive numbers) when the diaper 2 is appropriately worn. In the present embodiment, it is evaluated whether the size of the diaper 2 is appropriate or not, and whether the fastening tapes 20 are fastened at correct positions or not by using the stretch ratio R and the distance S.

For example, in the present embodiment, when the stretch ratio R is 75% and the distance S between the fastening tapes 20 satisfies h<S<j, it is evaluated that the wearing state of the diaper 2 is "appropriate".

When the stretch ratio R is 67%, and the distance S between the fastening tapes 20 is larger than j (S>j), the fastening positions of the fastening tapes 20 may be incorrect because the distance S is large despite improper stretch of the elastic members. The evaluation of the wearing state of the diaper 2 in such a case is that "the tapes should be fixed more inward".

When the stretch ratio R is 83% and the distance S between the fastening tapes 20 satisfies h<S<j, the evaluation of the wearing state of the diaper 2 is that "the diaper 2 is too small", because the elastic members are excessively stretched although the tapes are appropriately positioned.

In this way, in a case of the open-type disposable diaper such as the diaper 2, the evaluation of the type of diaper and the evaluation of the wearing method in the diaper 2 can be made based on the relationship between the stretch ratio R and the distance S. Consequently, the user of the terminal 110 can allow infants to wear the diaper more appropriately by using this evaluation method even if the wearing state of the diaper cannot be decided.

Other Embodiment

Although the embodiment of the present disclosure has been described as stated above, the aforementioned embodiments are for facilitating understanding of the present disclosure, and are not limiting of the present disclosure, and are not to be interpreted as limiting the present disclosure. The present disclosure can of course be altered and improved without departing from the gist thereof, and equivalents are intended to be embraced therein. For example, modifications as will be described below are possible.

In the aforementioned embodiment, the mark 6$m$ and the mark 26$m$ that are two-dimensional bar codes for specifying the type of disposable diaper are printed. However, the present disclosure is not limited thereto. The mark is not limited to the two-dimensional bar code, and other identifiers such as a usual linear bar code may be utilized.

As the other identifiers, the mark 6$m$ may be used as size notation of diaper. For example, by using a blue "M" mark provided as size notation of diaper, blue color may specify the product, and "M" may specify the size. Accordingly, a type for specifying the type of diaper is not required to be provided separately. This can reduce the number of operations and realize an easier evaluation.

The type of disposable diaper may be specified by using evaluation images such as the waist pattern 4B and the leg-surrounding pattern 4L, which include information for specifying the type of disposable diaper in advance. For example, the shape of pattern or the color of pattern may be changed for each type of diaper. Accordingly, identifiers for specifying the type of diaper are not required to be provided separately. This can reduce the number of operations and realize an easier evaluation.

Moreover, the specification of the type of disposable diaper may be performed by a direct input to the terminal 110 by a user of the terminal 110, or by displaying a selection screen on the terminal 110 to allow the user to select the type.

In the aforementioned embodiment, the waist pattern 4B and the leg-surrounding pattern 4L are printed by using a printer such as an inkjet printer. However, the present disclosure is not limited thereto. Printing methods such as offset printing and flexographic printing may be used appropriately.

Figure 9D:
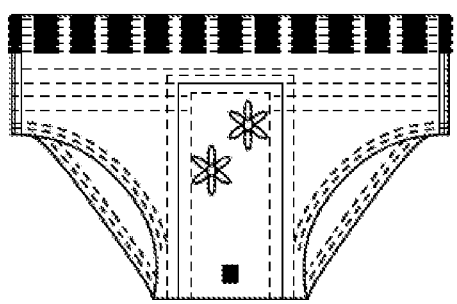
FIG. 9D is a diagram in a case where a part of waist elastic members 8B is colored.

Moreover, in the foregoing embodiment, the waist pattern 4B and the leg-surrounding pattern 4L are provided by printing the pattern of the diaper 1. However, the present disclosure is not limited thereto. FIG. 9D is a diagram in a case where apart of the waist elastic members 8B is colored. As illustrated in FIG. 9D, apart of the elastic members 8 may be colored, and the colored part of the elastic members 8 may be photographed as an evaluation target. In the present embodiment, although the elastic strings are used for the elastic members 8, elastic films, elastic nonwoven fabric or the like may also be used. Apart of or all of the elastic films or the elastic nonwoven fabric may be colored and photographed so that a pattern image (evaluation image) can be formed. Accordingly, the degree of deformation of the elastic members can be directly evaluated.

Moreover, in the foregoing embodiment, the pattern to be an object of photographing for an evaluation image (pattern image) is provided by printing the waist pattern 4B (leg-surrounding pattern 4L) on the waist portion (leg-surrounding portions) of the diaper 1. However, the present disclosure is not limited thereto. An image in which at least a part of the picture pattern 6d printed on the leak-proof sheet 6 is photographed maybe used as an evaluation image. This can evaluate the wearing state of the diaper without newly printing a pattern for evaluation on the diaper 1.

Moreover, in the foregoing embodiment, the distance P in the lateral direction from one vertex to another vertex of the actual wavy waist pattern 4B is calculated by using the distance T from the upper vertex to the lower vertex of the waveform of the waist pattern 4B, and the distance t on the image. However, the present disclosure is not limited thereto. The distance on the image and the actual distance may be compared by using one except the pattern such as the waist pattern 4B. For example, an actual distance U in the lengthwise direction from an upper end to a lower end of one of flower patters that are picture patterns 6d and a distance u on the image in the lengthwise direction from an upper end to a lower end of one of flower patters that are picture patterns 6d in FIG. 2A may be used for calculation. Accordingly, when the actual distance and the distance on the image are compared by using the part except the pattern used for evaluating the degree of elasticity, the pattern used for evaluating the degree of elasticity does not necessarily have a length in the lengthwise direction.

Moreover, in the foregoing embodiment, the pattern image was acquired by photographing the diaper worn by the wearer as a still image. However, the present disclosure is not limited thereto. The diaper worn by the wearer is photographed as a moving image, and the server 102 may extract the pattern image from the moving image to evaluate it. If the subject moves a lot like infants, it may be difficult to acquire still images. Thus, the wearing state can be more easily evaluated by making moving images.

In the foregoing embodiment, the terminal 110 and the server 102 are communicated via the network 103, the server 102 performs each processing and data management as an evaluation unit, and the terminal 110 serves as a display, so that the terminal 110 and the server 102 are combined as a computer system. However, the present disclosure is not limited thereto. The terminal 110 and the server 102 may share processing and data management, respectively. Also, the terminal 110 may perform all processing and data management as a computer system.

The foregoing embodiment can be achieved in such a manner in which the program causes the computer system including a microprocessor to execute the above-mentioned various processing. In this case, all processing may be prepared as a program, or a part of processing may be processed by hardware and the remaining processing may be prepared as a program.

Furthermore, it is possible to provide a program to a computer by using a non-transitory computer readable medium storing an executable program thereon. Examples of the non-transitory computer readable medium include magnetic recording media (such as flexible disks, magnetic tapes, and hard disk drives), CD-ROM (Read Only Memory) or the like.

The target wearers of the diaper 1 according to the foregoing embodiment are infants. However, the present disclosure is not limited thereto. The target wearers may be adults.

The invention claimed is:

1. An evaluation method of a wearing state of a disposable diaper including an elastic region in a waist portion or leg-surrounding portions, the evaluation method comprising:
   an evaluation image acquiring process in which a terminal including a photographing function acquires an image including at least a part of the elastic region as an evaluation image in the wearing state of the disposable diaper; and
   an evaluation process of evaluating the wearing state of the disposable diaper based on a degree of deformation of the evaluation image,
   wherein the evaluation process includes evaluating
      whether or not a size of the disposable diaper is appropriate, or
      whether or not the disposable diaper is appropriately worn.

2. The evaluation method according to claim 1, wherein a pattern is provided in at least the part of the elastic region, and
   the terminal acquires an image including at least a part of the pattern as the evaluation image in the evaluation image acquiring process.

3. The evaluation method according to claim 2, wherein the disposable diaper includes a lengthwise direction and a lateral direction intersecting with the lengthwise direction, and
   the pattern is formed by repeating a predetermined design three times or more along the lateral direction.

4. The evaluation method according to claim 3, wherein the pattern is formed by repeating the predetermined design at a predetermined pitch, and the predetermined pitch is larger than a maximum pitch of wrinkles that are formed in the elastic region in a state in which the elastic region is contracted by a predetermined ratio with respect to a maximum stretched state.

5. The evaluation method according to claim 2, wherein elastic members are provided in the elastic region, and
the pattern includes a plurality of colored portions provided in the elastic members.

6. The evaluation method according to claim 2, wherein the disposable diaper includes a lengthwise direction and a lateral direction intersecting with the lengthwise direction, and
the pattern has a predetermined length in the lengthwise direction of the disposable diaper.

7. The evaluation method according to claim 2, wherein the disposable diaper includes a lengthwise direction and a lateral direction intersecting with the lengthwise direction,
the pattern including a first part that is disposed outside an absorbent body in the lateral direction of the disposable diaper, and
the image including the first part as the evaluation image is acquired in the evaluation image acquiring process.

8. The evaluation method according to claim 2, wherein the disposable diaper includes a lengthwise direction and a lateral direction intersecting with the lengthwise direction,
the pattern including a second part that is disposed on an upper side of an absorbent body in the lengthwise direction of the disposable diaper, and
the image including the second part as the evaluation image is acquired in the evaluation image acquiring process.

9. The evaluation method according to claim 2, wherein the disposable diaper includes a lengthwise direction and a lateral direction intersecting with the lengthwise direction,
the pattern including a third part that is disposed in each of upper portions of leg opening portions of the disposable diaper in the lengthwise direction of the disposable diaper, and
the image including the third part as the evaluation image is acquired in the evaluation image acquiring process.

10. The evaluation method according to claim 2, wherein the disposable diaper includes a lengthwise direction and a lateral direction intersecting with the lengthwise direction,
the pattern includes a predetermined design,
the predetermined design has a shape symmetric with respect to the lengthwise direction and the lateral direction of the disposable diaper in a state in which the elastic region is contracted by a predetermined ratio with respect to a maximum stretched state.

11. The evaluation method according to claim 2, wherein a picture pattern that is visibly recognizable through an exterior sheet is provided in a leak-proof sheet provided on a skin side of the exterior sheet disposed on the most non-skin side of the disposable diaper, and
an image including at least a part of the picture pattern is acquired as the evaluation image in the evaluation image acquiring process.

12. The evaluation method according to claim 2, wherein the pattern is provided on an exterior sheet disposed on the most non-skin side of the disposable diaper, and
a picture pattern that is visibly recognizable through the exterior sheet is provided on a leak-proof sheet provided on a skin side of the exterior sheet.

13. The evaluation method according to claim 2, wherein the pattern includes information for specifying a type of the disposable diaper, and
the type of the disposable diaper is specified using the evaluation image.

14. The evaluation method according to claim 1, wherein in the evaluation image acquiring process, another image including at least a part of the elastic region as another evaluation image is acquired after the image including the evaluation image is acquired, and
the wearing state of the disposable diaper is evaluated based on degrees of deformation of the evaluation image and the other evaluation image.

15. The evaluation method according to claim 1, wherein evaluation information for each type is provided in the disposable diaper, the evaluation information being used for evaluating the wearing state of the disposable diaper for the each type of the disposable diaper, and
the degree of deformation of the evaluation image is evaluated using the evaluation information in the evaluation process.

16. The evaluation method according to claim 15, wherein a mark for specifying a type of the disposable diaper is provided in the disposable diaper,
the method further includes a mark image acquiring process in which the terminal acquires a mark image including the mark, and
the degree of deformation of the evaluation image is evaluated in the evaluation process by using the evaluation information corresponding to the type specified by the mark image.

17. The evaluation method according to claim 16, wherein the disposable diaper includes an absorbent main body, and
in a thickness direction, the mark is provided at a position overlapping with the absorbent main body and a position in which an elastic member is not provided.

18. The evaluation method according to claim 1, wherein the disposable diaper includes a lengthwise direction and a lateral direction intersecting with the lengthwise direction,
the disposable diaper is an open-type disposable diaper including a first waist portion, a second waist portion and an absorbent main body,
a fastening tape is provided in each end portion in the lateral direction in the second waist portion,
a target region for allowing the fastening tape to be fastened is provided in the first waist portion, and
the evaluation process includes evaluating whether the fastening tape has been fastened to an appropriate position with respect to the target region based on the degree of deformation of the evaluation image.

19. The evaluation method according to claim 1, wherein the disposable diaper includes a lengthwise direction and a lateral direction intersecting with the lengthwise direction,
the disposable diaper is an open-type disposable diaper including a first waist portion, a second waist portion and an absorbent main body,
a fastening tape is provided in each end portion in the lateral direction in the second waist portion,
a target region for allowing the fastening tape to be fastened is provided in the first waist portion,
an image including a fastening position of the fastening tape with respect to the target region as a fastening image is acquired, and the wearing state of the disposable diaper is evaluated in the evaluation process based on the fastening position specified by the fastening image and the degree of deformation of the evaluation image.

20. An evaluation method of a wearing state of a disposable diaper including an elastic region in a waist portion or leg-surrounding portions, the evaluation method comprising:
- an evaluation image acquiring process in which a terminal including a photographing function acquires an image including at least a part of the elastic region as an evaluation image in the wearing state of the disposable diaper; and
- an evaluation process of evaluating the wearing state of the disposable diaper based on a degree of deformation of the evaluation image,
- wherein
- an elapsed time since the wearer had a meal is acquired, and
- the wearing state of the disposable diaper is evaluated based on the degree of deformation of the evaluation image and the elapsed time.

21. An evaluation system of a wearing state of a disposable diaper including an elastic region in a waist portion or leg-surrounding portions, the evaluation system comprising:
- a terminal including a camera configured to acquire an image including at least a part of the elastic region as an evaluation image in the wearing state of the disposable diaper, and
- a processor configured to perform an evaluation process to evaluate the wearing state of the disposable diaper based on a degree of deformation of the evaluation image,
- wherein the evaluation process includes evaluating
  - whether or not a size of the disposable diaper is appropriate, or
  - whether or not the disposable diaper is appropriately worn.

22. A non-transitory computer-readable storage medium containing a program for evaluating a wearing state of a disposable diaper including an elastic region in a waist portion or leg-surrounding portions, the program, when executed by a computer system including a terminal that has at least a photographing function, instructing the computer system to perform:
- an evaluation image acquiring process of acquiring an image including at least a part of the elastic region as an evaluation image in the wearing state of the disposable diaper; and
- an evaluation process of evaluating the wearing state of the disposable diaper based on a degree of deformation of the evaluation image,
- wherein the evaluation process includes evaluating
  - whether or not a size of the disposable diaper is appropriate, or
  - whether or not the disposable diaper is appropriately worn.

* * * * *